US012648798B2

(12) United States Patent
Gandhi et al.

(10) Patent No.: US 12,648,798 B2
(45) Date of Patent: Jun. 9, 2026

(54) SYSTEMS FOR ATTENUATION OF INCREASED SPINAL FLEXION LOADS POST-FUSION AND ASSOCIATED METHODS

(71) Applicant: Highridge Medical, LLC, Westminster, CO (US)

(72) Inventors: Anup Gandhi, Superior, CO (US); Jason Inzana, Westminster, CO (US); John Caridi, Westminster, CO (US); Samuel Cho, Westminster, CO (US)

(73) Assignee: Highridge Medical, LLC, Westminster, CO (US)

( * ) Notice: Subject to any disclaimer, the term of this patent is extended or adjusted under 35 U.S.C. 154(b) by 301 days.

(21) Appl. No.: 17/723,753

(22) Filed: Apr. 19, 2022

(65) Prior Publication Data

US 2022/0233217 A1     Jul. 28, 2022

Related U.S. Application Data

(62) Division of application No. 16/275,751, filed on Feb. 14, 2019, now Pat. No. 11,344,337.
(Continued)

(51) Int. Cl.
*A61B 17/70* (2006.01)
*A61B 17/88* (2006.01)

(52) U.S. Cl.
CPC ...... *A61B 17/7053* (2013.01); *A61B 17/7001* (2013.01); *A61B 17/7002* (2013.01); *A61B 17/7011* (2013.01); *A61B 17/7022* (2013.01); *A61B 17/7031* (2013.01); *A61B 17/7032* (2013.01); *A61B 17/7043* (2013.01); *A61B 17/7049* (2013.01); *A61B 17/7062* (2013.01);
(Continued)

(58) Field of Classification Search
CPC ............ A61B 17/7053; A61B 17/7011; A61B 17/7032; A61B 17/7083
See application file for complete search history.

(56) References Cited

U.S. PATENT DOCUMENTS 8,740,941 B2    6/2014  Thramann
10,758,274 B1 *  9/2020  Bess .................. A61B 17/7053
(Continued)

FOREIGN PATENT DOCUMENTS

EP           2723260       4/2014
WO    WO 2016/166448    10/2016

OTHER PUBLICATIONS

Official Action for European Patent Application No. 19158113.1, dated Sep. 18, 2023 6 pages.
(Continued)

*Primary Examiner* — Nicholas J Plionis

(57) ABSTRACT

Implementations described herein include devices and systems for attenuation of increased spinal flexion loads post-fusion that include a transition member. The transition member may have a tension component coupleable to a fused vertebra of a plurality of fused vertebra of a fusion implant and to an adjacent unfused vertebra. The tension component may be tensionable to a selected value. The tension component may modulate a flexion range of motion of the adjacent unfused vertebra as a function of the selected value of tension of the tension component. The transition member may attenuate spinal flexion loads on adjacent unfused vertebra post-operatively.

12 Claims, 14 Drawing Sheets

2-Level Sublaminar Band
T9-10: 250 N
T10-11: 350 N

Related U.S. Application Data

(60) Provisional application No. 62/632,039, filed on Feb. 19, 2018.

(52) U.S. Cl.
CPC ...... *A61B 17/7083* (2013.01); *A61B 17/8869* (2013.01); *A61B 17/7067* (2013.01); *A61B 17/707* (2013.01)

(56) References Cited

U.S. PATENT DOCUMENTS

| | | | |
|---|---|---|---|
| 11,344,337 | B2 | 5/2022 | Gandhi et al. |
| 2008/0021466 | A1 | 1/2008 | Shadduck et al. |
| 2009/0024165 | A1 | 1/2009 | Ferree |
| 2009/0105715 | A1 | 4/2009 | Belliard et al. |
| 2009/0264932 | A1 | 10/2009 | Alamin et al. |
| 2011/0245875 | A1 | 10/2011 | Karim |
| 2013/0261668 | A1* | 10/2013 | Douget .............. A61B 17/7032 606/279 |
| 2014/0012326 | A1* | 1/2014 | Alamin .............. A61B 17/7055 606/279 |
| 2014/0094851 | A1 | 4/2014 | Gordon |
| 2016/0235447 | A1 | 8/2016 | Mundis, Jr. et al. |
| 2016/0242825 | A1 | 8/2016 | Simpson et al. |
| 2018/0078286 | A1 | 3/2018 | Le Couedic et al. |

OTHER PUBLICATIONS

Varlet, V, et al., "Junctional spinal disorders in operated adult spinal deformities: present understanding and future perspectives", Eur Spine J (2013) 22 (Suppl 2): S276-S295, (2013), 20 pgs.

Aubin, Carl-Eric, et al., "Instrumentation Strategies to Reduce the Risks of Proximal Junctional Kyphosis in Adult Scoliosis: A Detailed Biomechanical Analysis", Spine Deformity 3 (2015) 211e218, (2015), 8 pgs.

Bess, Shay, et al., "The effect of posterior polyester tethers on the biomechanics of proximal junctional kyphosis: a finite element analysis", J Neurosurg 2017: 26:125-133, (2016), 10 pgs.

Cahill, Patrick J., et al., "The use of a transition rod may prevent proximal junctional kyphosis in the thoracic spine after scoliosis surgery: a finite element analysis", SPINE vol. 37, No. 12, pp. E687-E695, (2012), 9 pgs.

Cammarata, Marco, et al, "Biomecanical risk factors for proximal junctional kyphosis: a detailed numerical analysis of surgical instrumentation variables", SPINE vol. 39, No. 8, pp. E500-E507, (2014), 8 pgs.

Cha, Jae-Ryong, et al., "Pedicle screw fixation and posterior fusion for lumbar degenerative diseases: effects on individual paraspinal muscles and lower back pain; a single-center, prospective study", BMC Musculoskeletal Disorders (2016) 17:63, (2016), 8 pgs.

Cho, Samuel K., "Proximal junctional kyphosis following adult spinal deformity surgery", Eur Spine J (2014) 23:2726-2736, (2014), 11 pgs.

Denis, Francis, et al., "Incidence and risk factors for proximal and distal junctional kyphosis following surgical treatment for Scheuermann kyphosis: minimum five-year follow-up", SPINE vol. 34, No. 20, pp. E729-E734, (2009), 6 pgs.

Glattes, R. Chris, et al., "Proximal junctional kyphosis in adult spinal deformity following long instrumented posterior spinal fusion: incidence, outcomes, and risk factor analysis", SPINE vol. 30, No. 14, pp. 1632-1649, (2005), 7 pgs.

Helgeson, Melvin D., "Evaluation of proximal junctional kyphosis in adolescent idiopathic scoliosis following pedicle screw, hook, or hybrid instrumentation", SPINE vol. 35, No. 2, pp. 177-181, (2010), 5 pgs.

Hyun, Seung-Jae, et al., "Patients with proximal junctional kyphosis after stopping at thoracolumbar junction have lower muscularity, fatty degeneration at the thoracolumbar area"; Spine J 2016; 16:1095-1101, (2016), 7 pgs.

Kim, Dong-Yun, "Comparison of multifidus muscle atrophy and trunk extension muscle strength: percutaneous versus open pedicle screw fixation", SPINE vol. 30, No. 1, pp. 123-129, (2004), 7 pgs.

Kim, Han Jo, et al., "Combined anterior-posterior surgery is the most important risk factor for developing proximal junctional kyphosis in idiopathic scoliosis", Clin Orthop Relat Res (2012) 470:1633-1639, (2012), 7 pgs.

Kim, Han Jo, et al., "Patients with proximal junctional kyphosis requiring revision surgery have higher postoperative lumbar lordosis and larger sagittal balance corrections", SPINE vol. 39, No. 9, pp. E576-E580, (2014), 5 pgs.

Kim, Han Jo, et al., "Proximal junctional kyphosis as a distinct form of adjacent segment pathology after spinal deformity surgery: a systematic review", SPINE vol. 37, No. 22S, pp. S144-S164, (2012), 21 pgs.

Kim, Yongjung, et al., "Proximal junctional kyphosis in adolescent idiopathic scoliosis after 3 different types of posterior segmental spinal instrumentation and fusions: incidence and risk factor analysis of 410 cases", SPINE vol. 32, No. 24, pp. 2731-2738, (2007), 8 pgs.

Kim, Yongjung, et al., "Proximal junctional kyphosis in adolescent idiopathic scoliosis following segmental posterior spinal instrumentation and fusion: minimum 5-year follow-up". SPINE vol. 30, No. 18, pp. 2045-2050, (2005), 6 pgs.

Lai, Po-Liang, et al., "Relation between laminectomy and development of adjacent segment instability after lumbar fusion with pedicle fixation", SPINE vol. 29, No. 22, pp. 2527-2532, (2004), 6 pgs.

Lau, Darryl, et al., "Proximal junctional kyphosis and failure after spinal deformity surgery: a systematic review of the literature as a background to classification development", SPINE vol. 39, No. 25, pp. 2093-2102, (2014), 10 pgs.

Liebsch, Christian, et al., "The rib cage stabilizes U1e t1uman U10racic spine: An in vitro study using stepwise reduction of rib cage structures", PloS one 2017; 12: e0178733, (2017), 13 pgs.

Mayer, Tom G., et al., "Comparison of CT scan muscle measurements and isokinetic trunk strength in postoperative patients", Spine 1989; 14:33-36, (1989), 4 pgs.

Mcgill, Stuart M., "Estimation of force and extensor moment contributions of the disc and ligaments at L4-L5", Spine 1988; 13:1395-1402, (1988), 8 pgs.

Metzger, Melodie F., et al., "Biomechanical Analysis of the Proximal Adjacent Segment after Multilevel Instrumentation of the Thoracic Spine: Do Hooks Ease the Transition?", Global Spine J 2016;6:335-343., (2016), 9 pgs.

Panjabi, Manohar, et al., "Physiologic strains in the lumbar spinal ligaments. An in vitro biomechanical study 1981 Volvo Award in Biomechanics", Spine 1982; 7:192-203, (1982), 12 pgs.

Scheer, Justin, et al., "Development of Validated Computer-based Preoperative Predictive Model for Proximal Junction Failure (PJF) or Clinically Significant PJK with 86% Accuracy Based on 510 ASD Patients With 2-year Follow-up", Spine 2016; 41: E1328-E1335, {2016}, 8 pgs.

Thawrani, Dinesh P., et al., "Transverse process hooks at upper instrumented vertebra provide more gradual motion transition than pedicle screws", SPINE vol. 39, No. 14, pp. E826 -E832, (2014), 7 pgs.

Theologis, Alexander A, et al., "Economic Impact of Revision Surgery for Proximal Junctional Failure After Adult Spinal Deformity Surgery: A Cost Analysis of 57 Operations in a 10-year Experience at a Major Deformity Center", SPINE vol. 41, No. 16, pp. E964-E972, (2016), 9 pgs.

Yagi, Mitsuru, et al., "Incidence, risk factors, and natural course of proximal junctional kyphosis: surgical outcomes review of adult idiopathic scoliosis. Minimum 5 years of follow-up", SPINE vol. 37, No. 17, pp. 1479-1489, (2012), 11 pgs.

European Application Serial No. 19158113.1, Extended European Search Report mailed Jul. 18, 2019, 9 pgs.

European Application Serial No. 19158113.1, Response filed Feb. 20, 2020 to Extended European Search Report mailed Jul. 18, 2019, 10 pgs.

Official Action for U.S. Appl. No. 16/275,751, dated Dec. 7, 2020 8 pages, Restriction Requirement.

(56) References Cited

OTHER PUBLICATIONS

Official Action for U.S. Appl. No. 16/275,751, dated Feb. 23, 2021 15 pages.

Final Action for U.S. Appl. No. 16/275,751, dated Sep. 3, 2021 15 pages.

Notice of Allowance for U.S. Appl. No. 16/275,751, dated Jan. 19, 2022 12 pages.

Supplemental Notice of Allowance for U.S. Appl. No. 16/275,751, dated Feb. 28, 2022 4 pages.

Official Action for European Patent Application No. 19158113.1, dated Sep. 2, 2024 6 pages.

Invitation to Grant for European Patent Application No. 19158113. 1, dated May 13, 2025 9 pages.

* cited by examiner

300

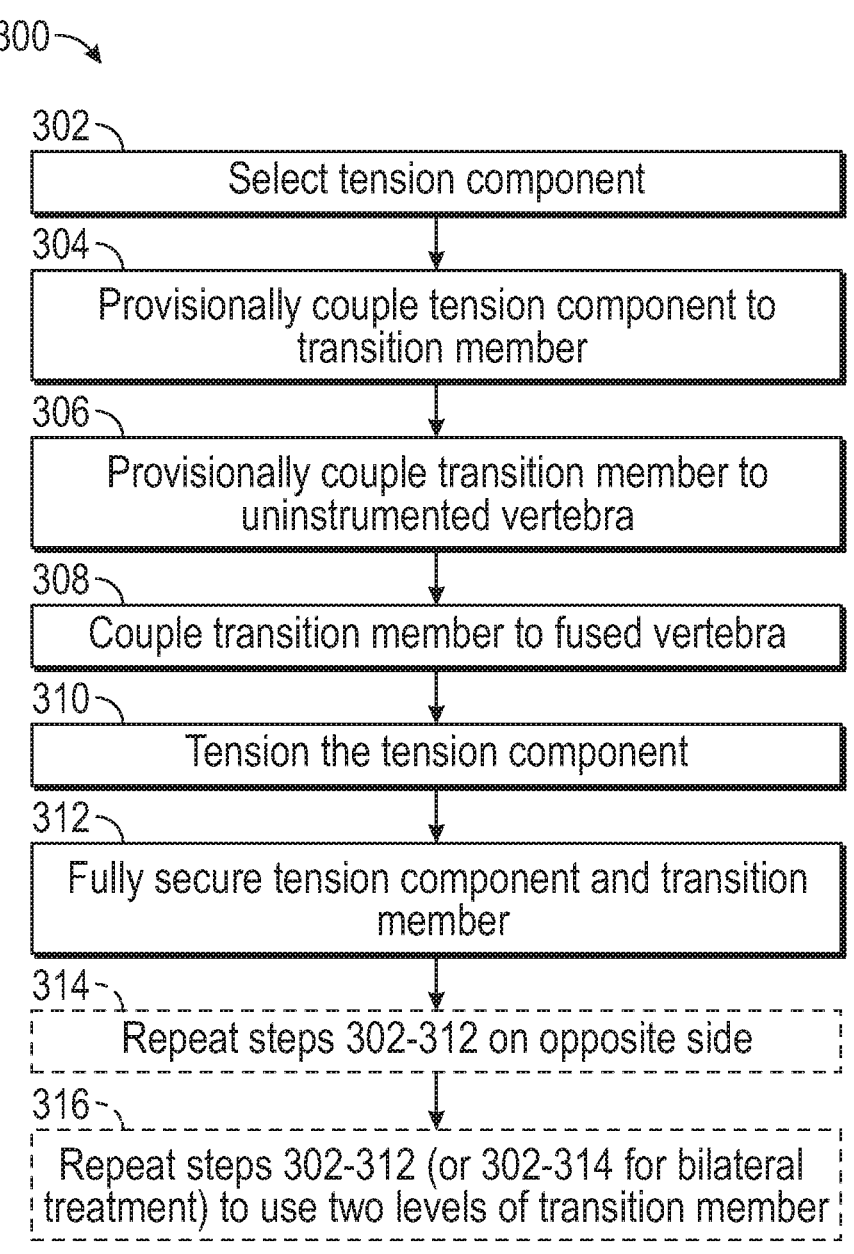

302 — Select tension component

304 — Provisionally couple tension component to transition member

306 — Provisionally couple transition member to uninstrumented vertebra

308 — Couple transition member to fused vertebra

310 — Tension the tension component

312 — Fully secure tension component and transition member

314 — Repeat steps 302-312 on opposite side

316 — Repeat steps 302-312 (or 302-314 for bilateral treatment) to use two levels of transition member

FIG. 3

SYSTEMS FOR ATTENUATION OF INCREASED SPINAL FLEXION LOADS POST-FUSION AND ASSOCIATED METHODS

CROSS REFERENCE TO RELATED APPLICATIONS

This application is a divisional of and claims benefit to U.S. patent application Ser. No. 16/275,751, filed on Feb. 14, 2019, which claims the benefit of U.S. Provisional Patent Application Ser. No. 62/632,039, filed on Feb. 19, 2018. The entire disclosures of the applications listed above are hereby incorporated by reference herein in their entirety.

BACKGROUND

Kyphosis is one example of a post-surgical complication following fusion of the spine that can lead to compromised patient outcomes and revision surgery. In one example, Proximal junctional kyphosis (PJK) can be defined as an increase in kyphosis of 10 degrees or more, relative to the preoperative measurements, between the inferior endplate of the uppermost instrumented vertebra (UIV) and the superior endplate of the vertebra two levels above the UIV. The reported incidence of PJK is significant and may lead to one or more of radiographic changes, aesthetic changes, back pain, disability, and, ultimately, proximal junction failure.

SUMMARY

Improving spinal fusion patient outcomes by attenuating hypermobilization that may be associated with increased post-operative flexion loads of the spine proximal to the terminal instrumented vertebra may be desirable. The present disclosure provides for various devices, systems, methods, and embodiments that may include a transition member used to attenuate hypermobilization in the spine proximal to instrumented vertebrae. The transition member may include a tension component coupleable to a fused vertebra of a plurality of fused vertebra or a fusion implant and to an adjacent unfused vertebra. The tension component may be tensionable to a selected value. The tension component may modulate a flexion range of motion of the adjacent unfused vertebra as a function of the selected value of tension of the tension component. The transition member may attenuate spinal flexion loads on the adjacent unfused vertebra post-operatively. The various devices, systems, methods, and embodiments may also include the fusion implant coupleable to the plurality of fused vertebra.

In another embodiment, the present disclosure provides for a method that may include steps such as selecting a tension component of a transition member, coupling the transition member to a fusion implant or an underlying instrumented vertebra, coupling the tension component to the transition member, tensioning the tension component to a selected value, coupling the tension component to an adjacent unfused vertebra, and modulating a flexion range of motion of the adjacent unfused vertebra with the transition member as a function of the selected value of tension of the tension component.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 is a flow chart illustrating one exemplary method according to the present disclosure.

DETAILED DESCRIPTION

Example embodiments will now be described more fully with reference to the accompanying drawings.

Spinal fusion involves immobilizing two or more vertebrae, to correct some form of deformity or degeneration, such as disc degeneration or correction of spondylosis. Implants such as pedicle screws and connecting rods are commonly used to secure the two or more vertebrae, while bone grows between the vertebral end plates. An interbody implant is also often used to maintain the space between the vertebral bodies and assist in encouraging bone growth. Spinal fusion reduces motion between the fused vertebrae, which is known to induce additional stresses on adjacent unfused vertebra. The present disclosure involves an implant, discussed herein as a transition member, to assist in transitioning some of the new loads experienced by the unfused vertebra onto the fusion implants, such as the connecting rods, screws or interspinous devices. As discussed in detail below, the transition member can include a clamp or similar mechanism secured to the fusion implants (e.g., the connecting rod) and a flexible member connected to an adjacent unfused vertebra and the clamp.

The present disclosure provides for various devices, systems, methods, and embodiments that may include a transition member. The transition member may include a tension component coupleable to a fused vertebra of a plurality of fused vertebra or a fusion implant and to an adjacent unfused vertebra. The tension component may be tensionable to a selected value. The tension component may modulate a flexion range of motion of the adjacent unfused vertebra as a function of the selected value of tension of the tension component. The transition member may attenuate spinal flexion loads on the adjacent unfused vertebra post-operatively, by transmitting a portion of the loads onto the fused vertebrae through the transition member. The various devices, systems, methods, and embodiments may also include the fusion implant(s) coupleable to the plurality of fused vertebra. Such devices, systems, methods, and embodiments may, among other things, improve spinal fusion patient outcomes by attenuating hypermobilization that may be associated with increased post-operative flexion loads of the spine proximal to the terminal instrumented vertebra. Attenuating hypermobilization by supporting the spine against increased flexion loads as an adjunct to fusion surgery may mitigate or prevent the development of post-surgical complications following fusion of the spine that may include proximal junctional kyphosis (PJK) and distal junctional kyphosis (DJK).

Figure 1B:
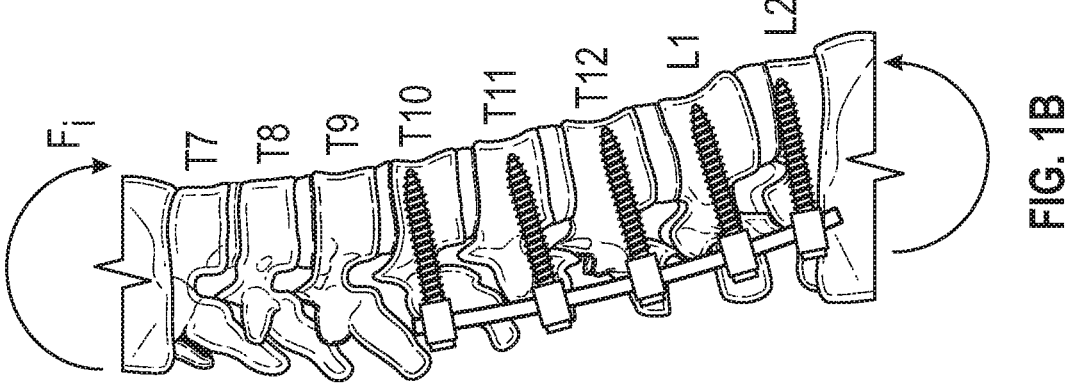
FIG. 1B illustrates a side, cut-away view of an increased flexion load on an instrumented spine that has undergone posterior fusion.
Figure 1A:
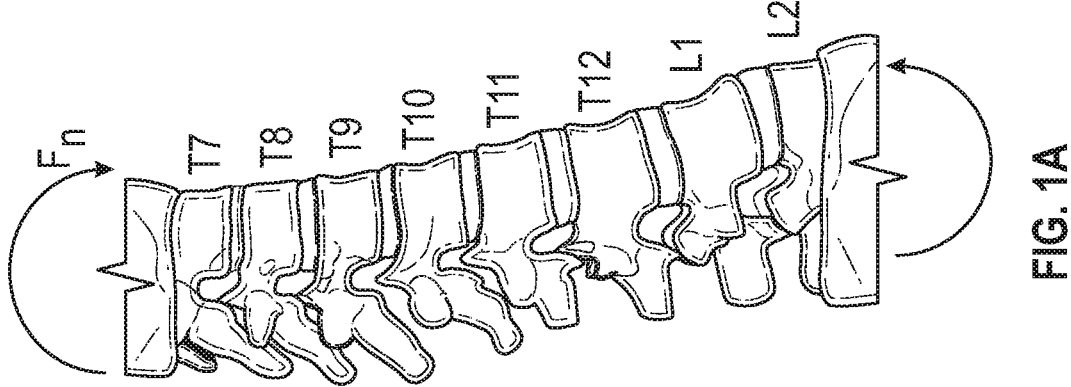
FIG. 1A illustrates a side, cut-away view of normal flexion load on an uninstrumented spine.

FIG. 1A illustrates a normal flexion load $F_n$ on an uninstrumented spine and FIG. 1B illustrates an increased flexion load $F_i$ on an instrumented spine that has undergone posterior fusion. The increased loading experienced by the instrumented spine may be due to the stiffness of the fusion implant (or fusion construct) or to iatrogenic damage to posterior ligament complex. Such increased loading can lead to hypermobility of the spine proximal to the terminal instrumented vertebra of the fusion implant.

Figure 2A:
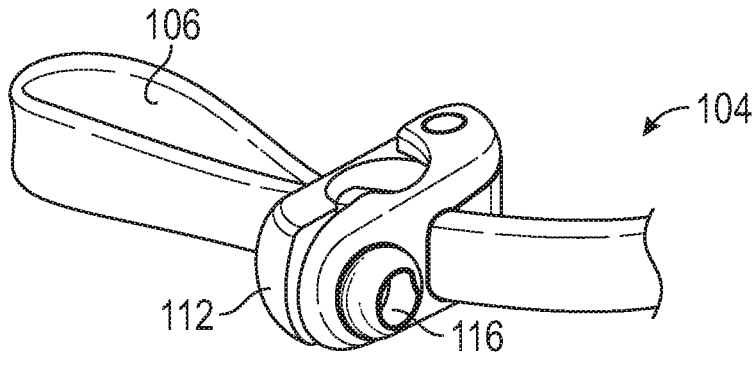
FIG. 2A is a perspective view of a first embodiment according to the present disclosure and FIG. 2B illustrates the embodiment of FIG. 2A in an operational configuration.

One example of a system 100 according to the present disclosure is illustrated in FIG. 2. The system 100 can include a fusion implant (or fusion construct) 102 coupleable to a plurality of fused vertebra and a transition member 104. The transition member 104 can include a tension component 106 coupleable to a fused vertebra 108 of the plurality of fused vertebra and an adjacent unfused vertebra 110. As will be discussed further below, the tension component 106 can include any suitable flexible elongate member, such as a tether, a cord, a band, or a flexible rod. (As used herein, the terms tethers, cords, and bands can be used interchangeably and simply refer to any suitable flexible, elongate member.) The tension component 106 can be tensionable to a selected value and can modulate a flexion range of motion (ROM) of the adjacent unfused vertebra 110 as a function of the selected value of tension of the tension component 106. One embodiment may have a tension value for the tension component 106 of in ranges including 200 to 400 Newtons (N) or 250 to 350 N, other ranges may be utilized. The transition member 104 can attenuate spinal flexion loads on the adjacent unfused vertebra 110 post-operatively by transferring at least a portion of the load through the transition member onto the fusion construct.

Furthermore, the system 100 can include a second transition member 104' identical to the first transition member 104 that is positioned opposite the first transition member 104 relative to the medial plane of the spine in order to effect bilateral attenuation of flexion loads on the adjacent unfused vertebra 110. Transition member 104 (or transition members 104, 104') can be configured to attenuate PJK or DJK of the adjacent unfused vertebra 110 based on whether the adjacent vertebra 110 is cranial or caudal to the underlying instrumented vertebra 108.

Figure 12:
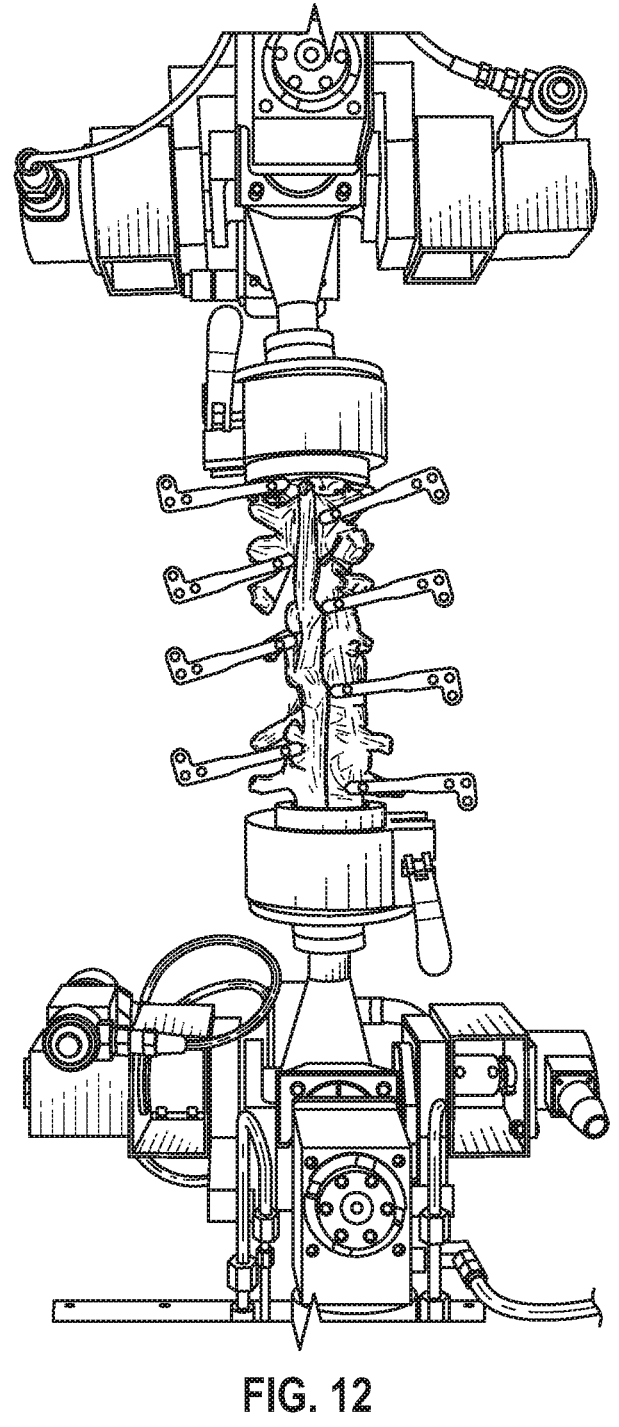
FIG. 12 illustrates certain aspects of the biomechanical test setup used to test the various spine specimen.

In one example, the transition member 104 can comprise a clamp 112 securable to a rod 114 of the fusion component 102 and to the tension component 106. Here, the tension component 106 can include any suitable flexible, elongate member that is tensionable to the selected value. In the example utilizing a flexible elongate member, the tension component 106 can be tensioned via a tensioning instrument, such as the one discussed below in reference to FIG. 12. In one example, the tension component 106 can be a polyester band. The tension component 106 can be coupleable to the adjacent unfused vertebra 110 sublaminarly or to a spinous process or to the transverse process of the adjacent unfused vertebra 110. The pedicle screw replacement Universal Clamp® implant distributed by Zimmer Biomet Spine, Inc. (Westminster, CO) can be used as a transition member with certain modifications in how the flexible member engages the vertebra.

FIG. 3 is a flowchart illustrating a method 300 according to an example embodiment. The method 300 can be performed as an adjunct to spinal fusion subsequent to implantation of a fusion implant 102, such as shown in FIG. 3. The method 300 can include operations such as selecting a tension component 106 of a transition member 104, coupling at least a portion of the transition member 104 to an underlying instrumented vertebra 108 of a plurality of underlying instrumented vertebra of a fusion implant 102, coupling the tension component 106 to the transition member 104, tensioning the tension component 106 to a selected value, coupling the tension component 104 to an adjacent unfused vertebra 110 under the selected value of tension, and modulating a flexion range of motion of the adjacent unfused vertebra 110 with the transition member 104 as a function of the selected value of tension of the tension component 106. The method 300 can also include provisionally coupling the tension component 106 to the adjacent unfused vertebra 110 prior to tensioning the tension component 106 to the selected value.

In an example, system 100 described above can be implanted as follows. The method 300 can begin at 302 with the selection of a tension component 106 of a transition member 104. In one example, the tension component 106 selected can be a polyester band and the transition member 104 can be a clamp. In another example, the tension component 106 can be a flexible rod.

At 304, the tension component 106 can be provisionally coupled to the transition member 104. In one example, a first end of the band can be threaded through an aperture in the clamp.

Figure 2B:
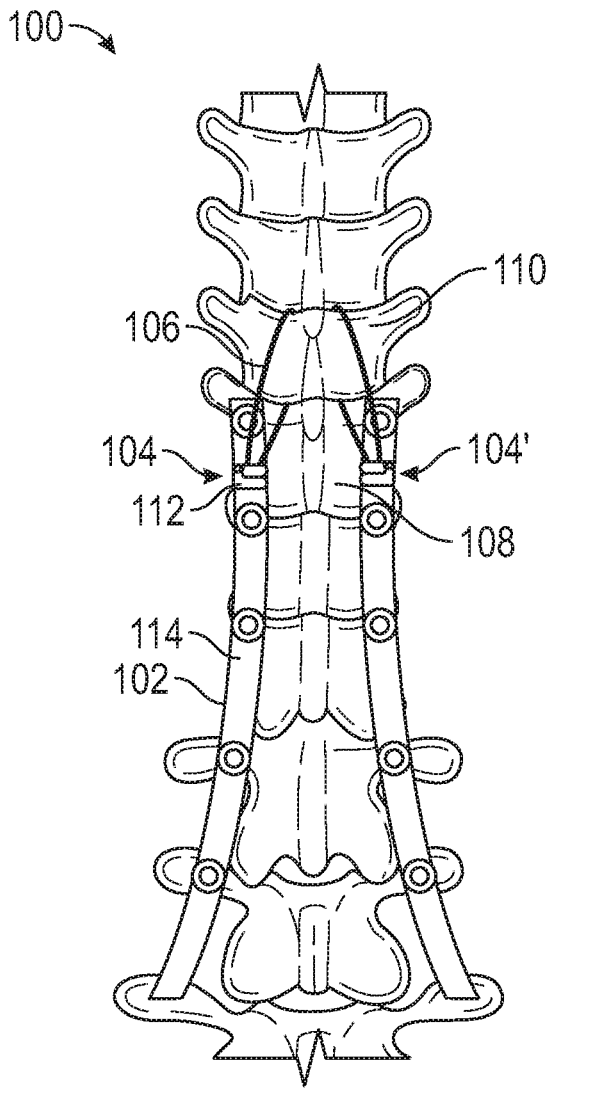
Figure 10:
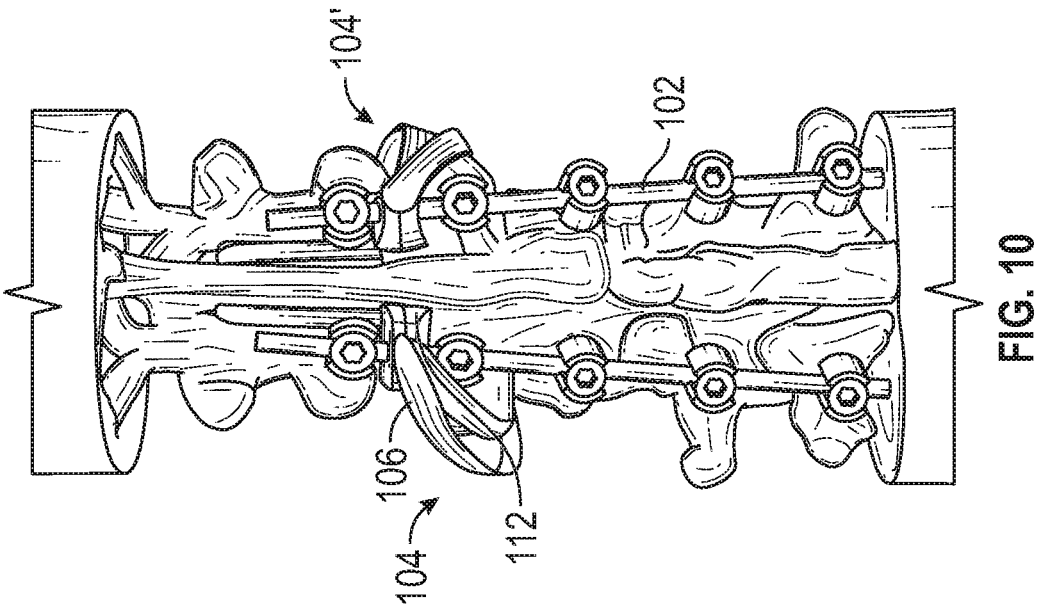
FIG. 10 illustrates a fused spine specimen also including a transition member according to an example embodiment.

At 306, the tension component 106 can be provisionally coupled to an adjacent uninstrumented vertebra 110. In one example, the band can be provisionally coupled to the adjacent uninstrumented vertebra 110 sublaminarly by extending a free second end the band from the clamp to the adjacent uninstrumented vertebra 110 and passing the free second end of the band under the lamina in a caudal-to-cephalad direction back to the clamp, where the second end can be coupled to the clamp. In another example, the band can be provisionally coupled to the adjacent uninstrumented vertebra 110 by passing a free second end of the band from the clamp around a transverse process of the adjacent uninstrumented vertebra 110 and back to the clamp, where the second end can be coupled to the clamp. In some examples, a second clamp can be used, and the second end is threaded into the second clamp. In such examples, the first clamp and second clamp can be positioned on opposing fusion constructs fixed along either side of a midline of the fused vertebrae (such as shown in FIGS. 2B and 10).

At 308, the transition member 104 can be coupled to a fused vertebra 108 of a plurality of fused vertebra of a fusion implant 102. In one example, the transition member 104 can be coupled to a rod of the fusion implant 102. The underlying vertebra 108 can be proximate the upper end or the lower end of the fusion implant 102 and on the same side of the fusion implant 102 as the adjacent uninstrumented vertebra 110.

Figure 13:
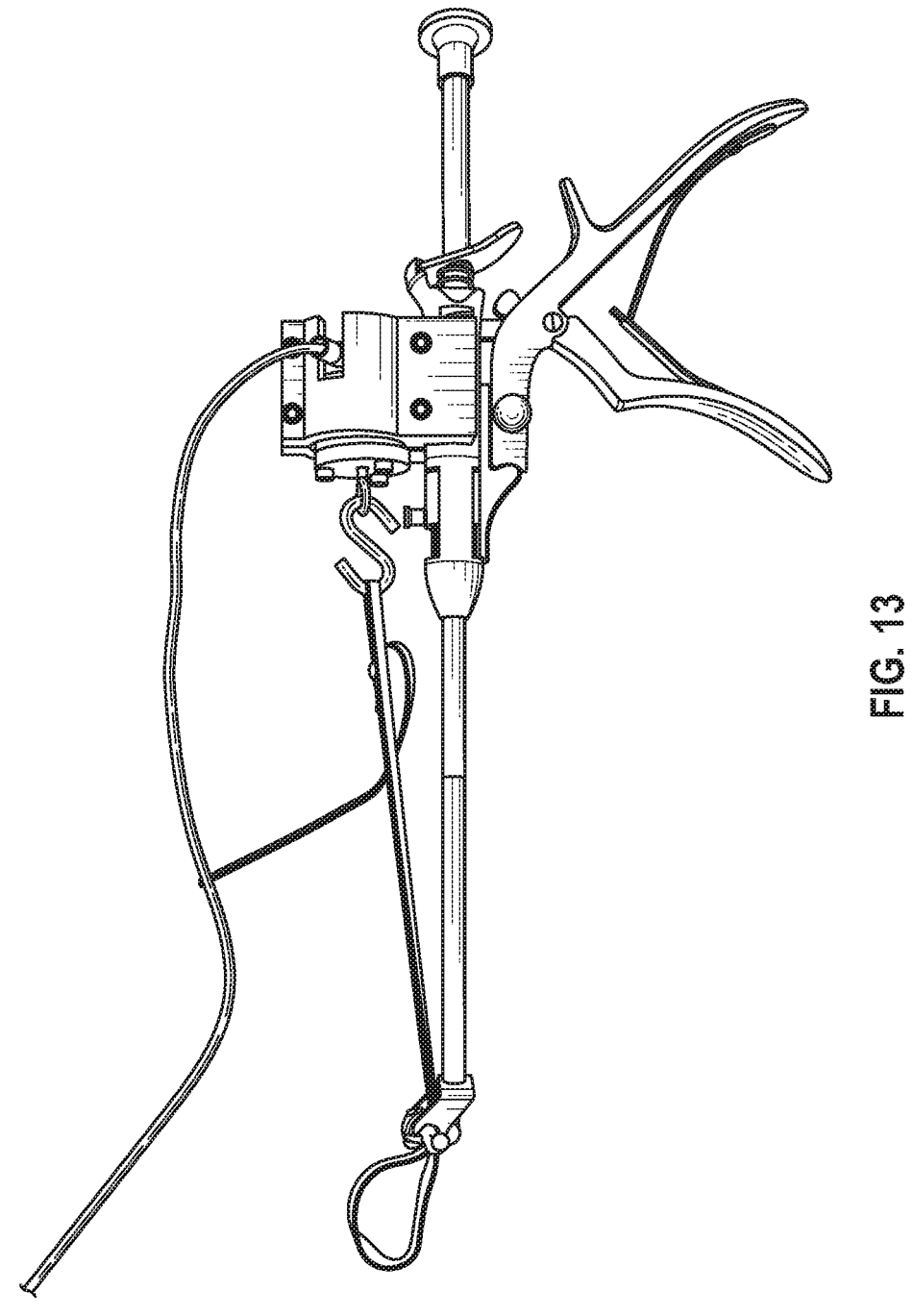
FIG. 13 shows an exemplary tensioner according to an example embodiment.

At 310, the tension component 106 can be tensioned to a selected value. In one example, a tensioner (such as the tensioner depicted in FIG. 13) can be used to tension the band by pulling at least one free end of the band through the clamp to reduce the length of the loop portion of the band coupled to the adjacent uninstrumented vertebra 110. In an example, the selected value of tension can be within ranges such as from 200 to 400 N or from 250 to 350 N. However, a skilled artisan will appreciate that different selected values can be desirable based on a number of additional factors such as, but not limited to, the characteristics of the selected tension component 106 and the weight of the patient.

Figures 4, 5, 6:
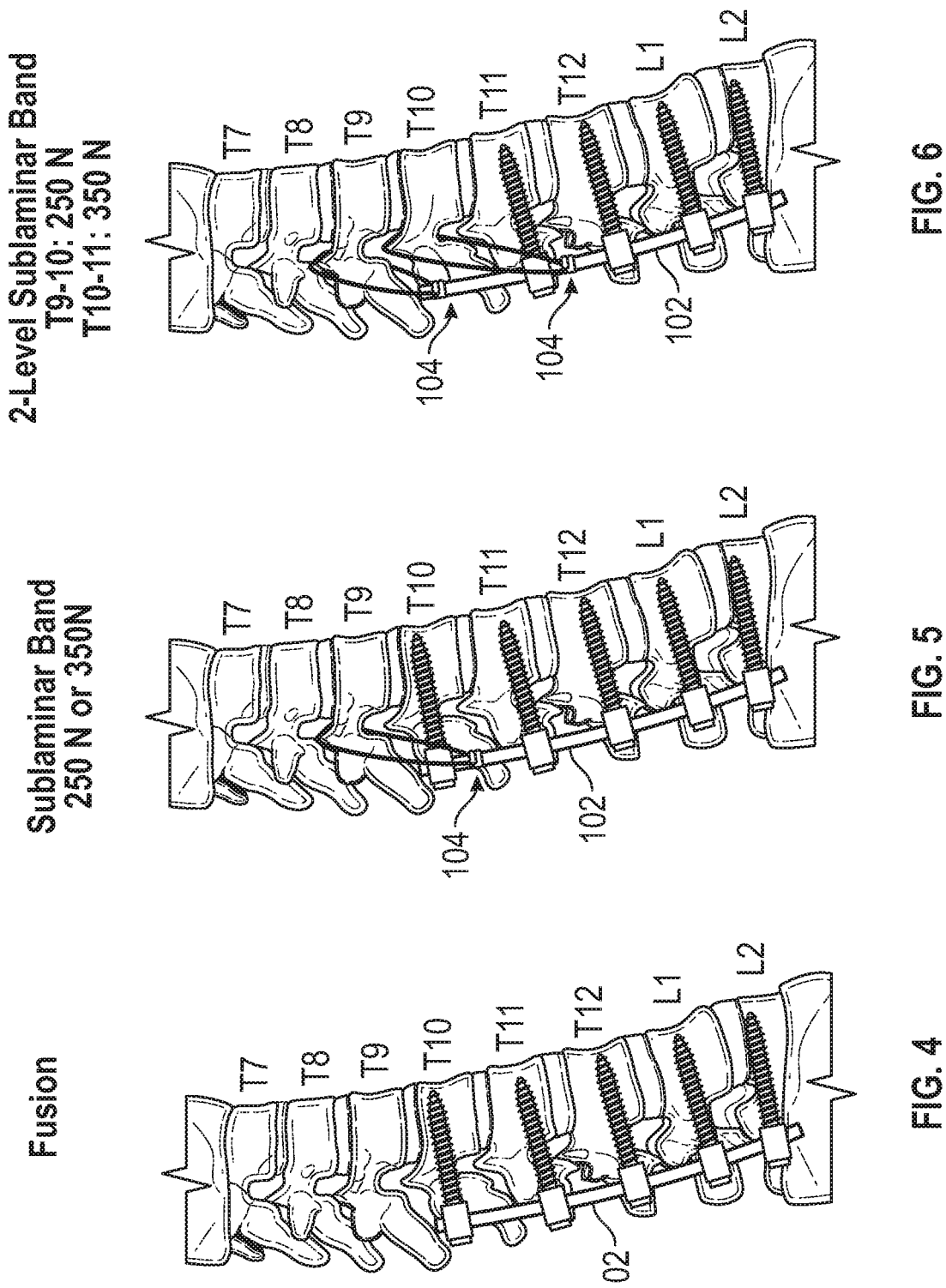
FIG. 4 is a schematic, side, cut-away view of a fused spine.
FIG. 5 is a schematic, side, cut-away view of a fused spine including a transition member according to an exemplary embodiment.
FIG. 6 is a schematic of a fused spine including two transition members according to an exemplary embodiment.

At 312, the tension component 106 can be secured under the selected value of tension and the transition member 104 can be fully secured to the fusion implant 102 in a final operative configuration as illustrated in FIG. 5. In one example, a set screw 116 can be advanced into the clamp to secure the band within the clamp and secure the clamp to the rod. Accordingly, a flexion range of motion of the adjacent unfused vertebra 110 can be modulated with the transition member 104 as a function of the selected value of tension of the tension component 106. The flexion range of motion of the adjacent unfused vertebra 110 can be modulated to attenuate proximal junction kyphosis or distal junction kyphosis (as the case may be) of the adjacent unfused vertebra 110.

At 314, method steps 302-312 can optionally be repeated on the opposite side of the spine to effect bilateral treatment.

At 316, method steps 302-314 can optionally be repeated to further modulate the flexion range of motion of the adjacent uninstrumented vertebra 110 by coupling a second fused vertebra of the plurality of fused vertebra of the fusion implant to the underlying vertebra 108 as illustrated in FIG. 6.

In a second example illustrated in FIGS. 17A and 17B, a system 200 can be similar to the system 100 described above but with a number of key differences discussed below. The transition member 204 can comprise a tension component 206 coupleable to a fused vertebra 208 of the plurality of fused vertebra and an adjacent unfused vertebra 210. The tension component 206 can comprise any suitable flexible elongate member, such as a tether, a cord, a band, or a flexible rod. The transition member 204 can further comprise a first bone implant 212 and a second bone implant 214. The first bone implant 212 can be engageable in one of the underlying vertebra 208 and the adjacent unfused vertebra 210, while the second bone implant 214 can be engageable in the other one of the two vertebrae. The first bone implant 212 can receive a first end of the tension component 206 and, either prior to, during, or subsequent to tensioning the tension component 206 to the selected value, the second bone implant 214 can receive a second end of the tension component 206 (or vice versa). A set screw or other fastener can secure the first and second ends of the tension component 206 under tension in the respective first and second bone implants 212, 214. Furthermore, the system 200 can comprise a second transition member 204' identical to the first transition member 204 that is positioned opposite the first transition member 204 relative to the medial plane of the spine in order to effect bilateral attenuation of flexion loads on the adjacent unfused vertebra 210. The devices, systems, and methods described in U.S. Provisional Patent Application 62/551,845, filed on August 2017 and hereby incorporated by reference in its entirety, can be used as a transition member in accordance with the techniques discussed herein.

In an example, system 200 described above can be implanted in accordance with method 400, which includes operations as follows. The method 400 can begin at 402 with the selection of a tension component 206 of a transition member 204. In one example, the tension component 206 selected can be a cord. In another example, the tension component 106 can be a flexible rod.

At 404, a first bone implant 212 can be implanted in either the underlying vertebra 208 or the adjacent unfused vertebra 210. In one example, the first bone implant and the second bone implant 214 can each comprise pedicle screws.

At 406, a second bone implant 214 can be implanted in the remaining one of the underlying vertebra 208 and the adjacent unfused vertebra 210.

At 408, the first end of the tension component 206 can be coupled to either one of the first bone implant 212 and the second bone implant 214.

At 410, the tension component 406 can be tensioned to a selected value. In one example, a tensioner (such as the tensioner depicted in FIG. 13) can be used to tension the tension component by pulling a free end of the tension component until the tension component is tensioned to a selected value. In an example, the selected value of tension can be within ranges such as from 200 to 400 N or from 250 to 350 N. However, a skilled artisan will appreciate that different selected values can be desirable based on a number of additional factors such as, but not limited to, the characteristics of the selected tension component 206 and the weight of the patient.

Figures 17A, 17B:
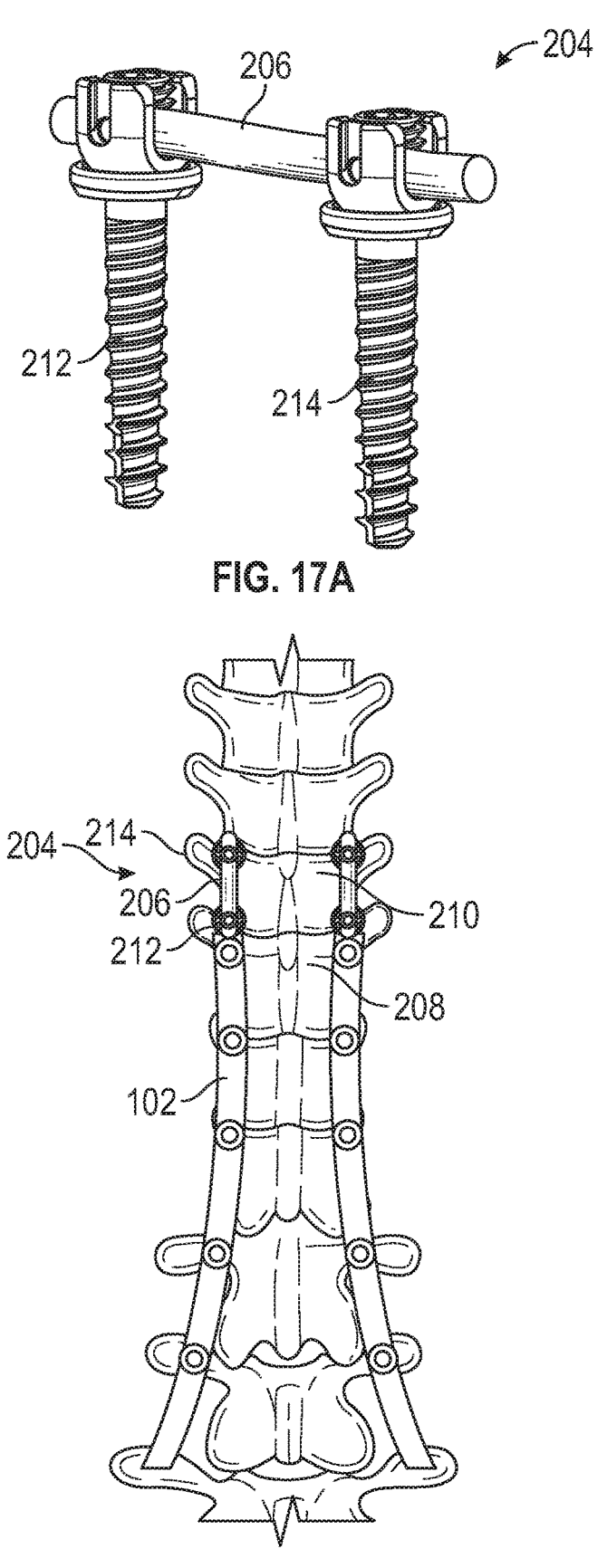
FIG. 17A is a perspective view of a first embodiment according to the present disclosure and FIG. 17B illustrates the embodiment of FIG. 17A in an operational configuration.
Figure 18:
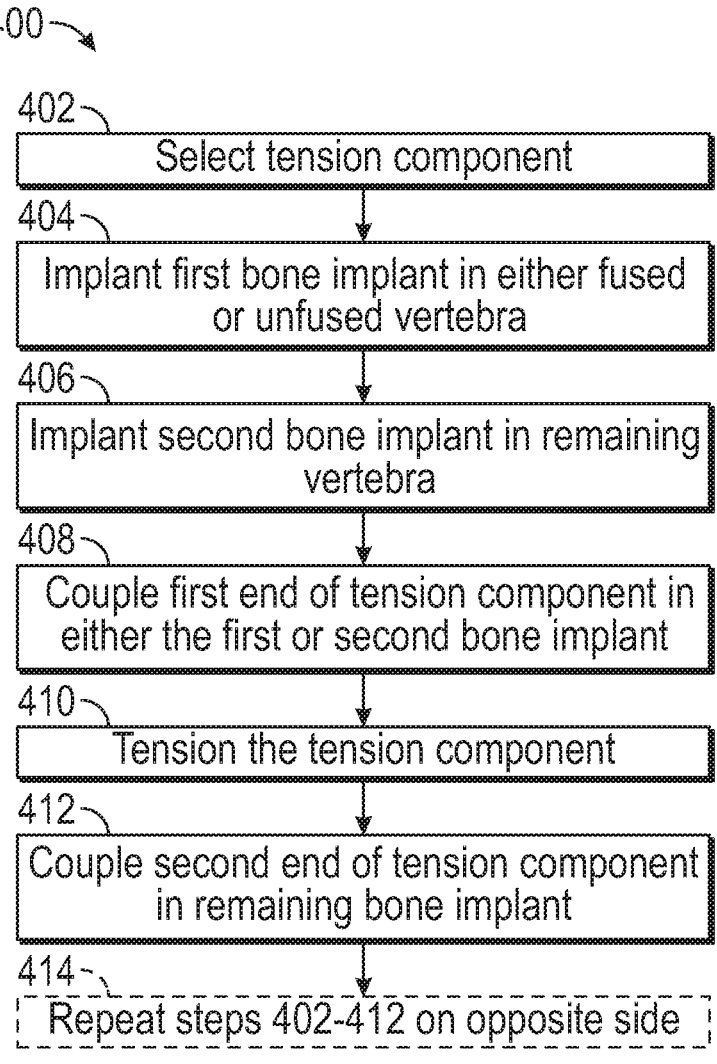
FIG. 18 is a flow chart illustrating another exemplary method according to the present disclosure.

At 412, the first end of the tension component 206 can be coupled to either one of the first bone implant 212 and the second bone implant 214 in a final operative configuration as illustrated in FIG. 17B. Accordingly, a flexion range of motion of the adjacent unfused vertebra 210 can be modulated with the transition member 204 as a function of the selected value of tension of the tension component 206. The flexion range of motion of the adjacent unfused vertebra 210 can be modulated to attenuate proximal junction kyphosis or distal junction kyphosis (as the case may be) of the adjacent unfused vertebra 210.

At 414, method steps 402-412 can optionally be repeated on the opposite side of the spine to effect bilateral treatment.

Experimental Data

Figure 9:
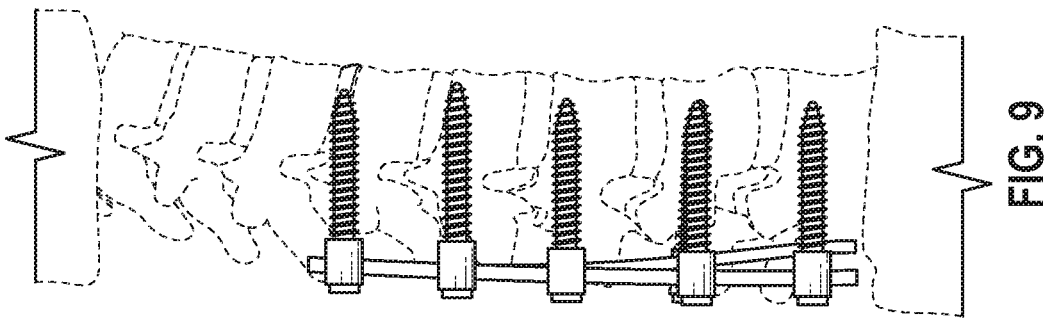
FIG. 9 is a radiographic representation of the fused spine specimen of FIG. 8.
Figure 8:
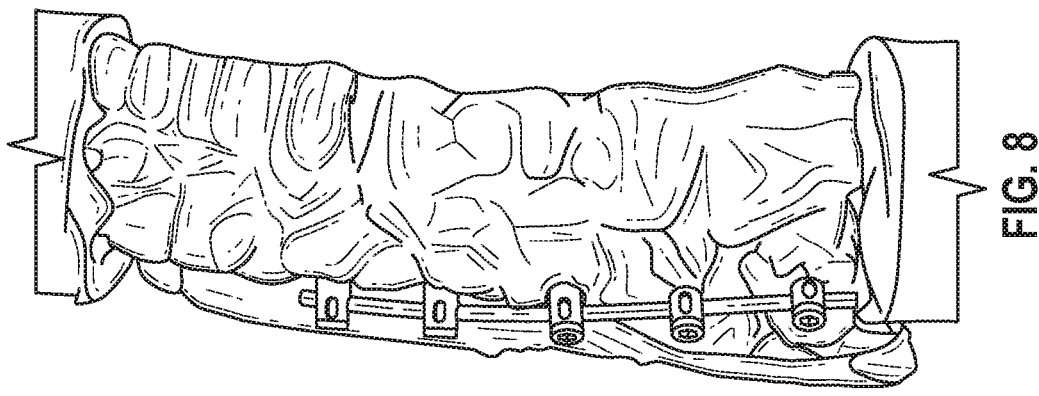
FIG. 8 illustrates a perspective side view of a fused spine specimen.
Figure 7:
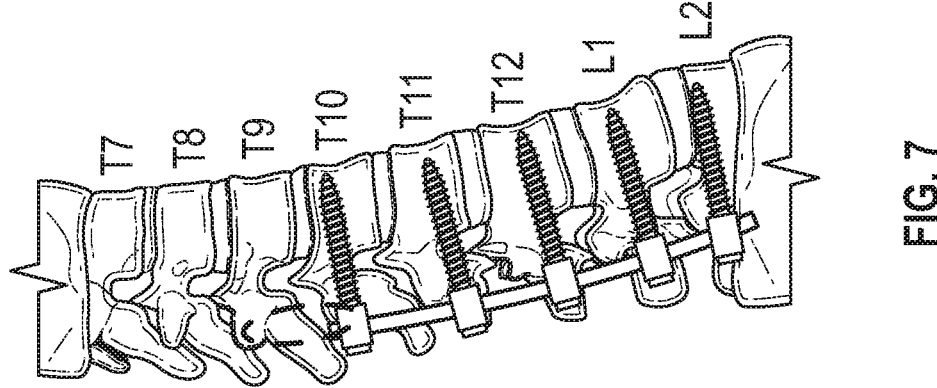
FIG. 7 is a schematic of a fused spine including a hand tied suture loop.

A study conducted by the inventors of the present disclosure illustrates the efficacy of the examples and embodiments of the present disclosure. The following data demonstrate that use of a transition member adjunct to a spinal fusion can modulate the biomechanical flexion range of motion (ROM) as a function of the tension applied to the band and can effectively attenuate hypermobilization. Also, the level of attenuation can be easily tuned based on the tension applied to the band. Eight human cadaveric thoracolumbar spines were dissected of soft tissue, preserving the osseoligamentous tissues and intervertebral discs, and the T7-L2 segment was isolated. The end vertebrae (T7 and L2) were partially embedded in polymethyl methacrylate (PMMA) bone cement, leaving the discs and ligaments exposed. Small screws were placed in the ventral cortex of each vertebral body, lateral to the anterior longitudinal ligament (ALL), for rigid attachment of 3D motion tracking markers. (See FIGS. 8, 9, and 12).

Figure 11:
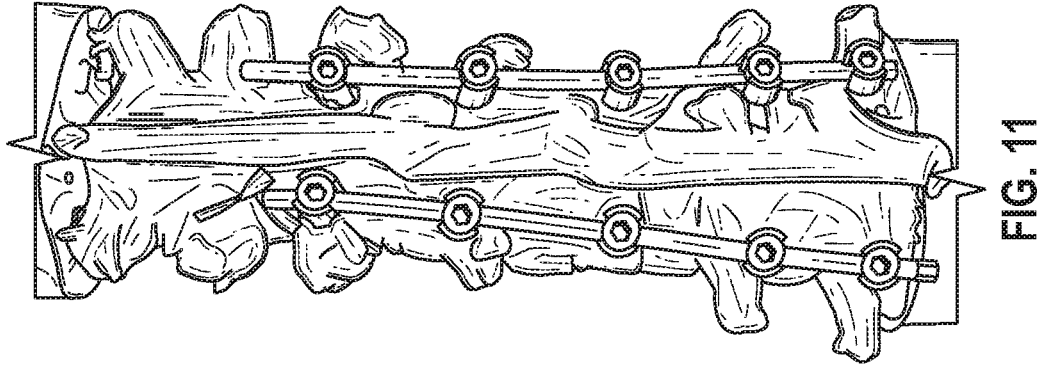
FIG. 11 illustrates a fused spine specimen with a hand tied suture loop.

With reference to FIGS. 4-7 and FIGS. 8-12, spine specimens were prepared and then instrumented by bilateral placement of pedicle screws at each fusion level (T10-L2) and the pedicle screws were connected with a 5.5 mm stainless steel rod. Each specimen was tested under seven conditions: native spine (Native), fused spine (Fused), fused spine plus bilateral clamps having sublaminar tethers tensioned to 250 N at T9-T10 (Tethers 250 N); fused spine plus bilateral clamps having sublaminar tethers tensioned to 350 N at T9-T10 (Tethers 350 N); fused spine plus bilateral clamps having sublaminar tethers tensioned to 250 N at T9-T10 and 350 N at T10-T11 (2 Level Tethers);

Prior to each biomechanical test, radiographs of each instrumented condition were collected using a C-arm (OEC 9900 Elite; GE Healthcare, Chicago, IL) to measure changes in the lordotic angle at T9-T10 that may have been induced by tensioning the tethers or suture loop. Each specimen was pre-conditioned through 3 cycles of pure moment loading in flexion-extension (FE), lateral bending (LB), and axial rotation (AR) at 4 Nm followed by 8 Nm prior to testing using a servo-hydraulic axial/torsional test frame with dual Bionix® Spine Subsystem attachments (FIG. 11). The caudal Spine Subsystem was mounted to a passive XY table to eliminate shear and a 10 N axial compressive load was maintained throughout testing to avoid tension. Three cycles of 4 Nm moments were applied to the native spine in FE, LB, and AR. For each instrumentation step, the specimens were loaded to 8 Nm in FE, LB, and AR in 3 cycles each to simulate an increase in loading following pedicle screw instrumentation. The relative rotations of each motion segment were recorded through a 3D motion tracking system and the Euler angles were exported for each principal.

Rotational data from the third loading cycle in each principal direction was used for analysis. LOESS filtering, with a smoothing factor of 0.01, was used to remove noise from the rotation-time data. The maximum rotations of each motion segment were then extracted to determine the range of motion (ROM) for each principal direction and normalized to the motion of the native spine loaded at 4 Nm. At the levels proximal to the fusion (T7-T10), the ROM data were analyzed using two-way repeated measures ANOVA and Dunnett's test for post-hoc comparisons. Changes in the lordotic angle at T9-T10 with each intervention relative to the Fused condition were calculated and a one-sample t-test was used to check if these changes were significantly different from zero. All data satisfied assumptions of normality according to the Shapiro-Wilk test. Statistics were performed in Prism software and differences were considered statistically significant for $p<0.05$.

Changes in Sagittal Alignment

The mean change in lordosis at T9-T10 with the tethers tightened to 250 N and 350 N compared to the Fused condition was $0.7\pm0.6$ degrees and $1.0\pm0.8$ degrees, respectively. The 2-level Tethers resulted in mean changes of $0.5\pm0.5$ degrees. Each of these changes was significantly different from zero ($p<0.05$).

Flexion-Extension Range of Motion

Figure 14A:
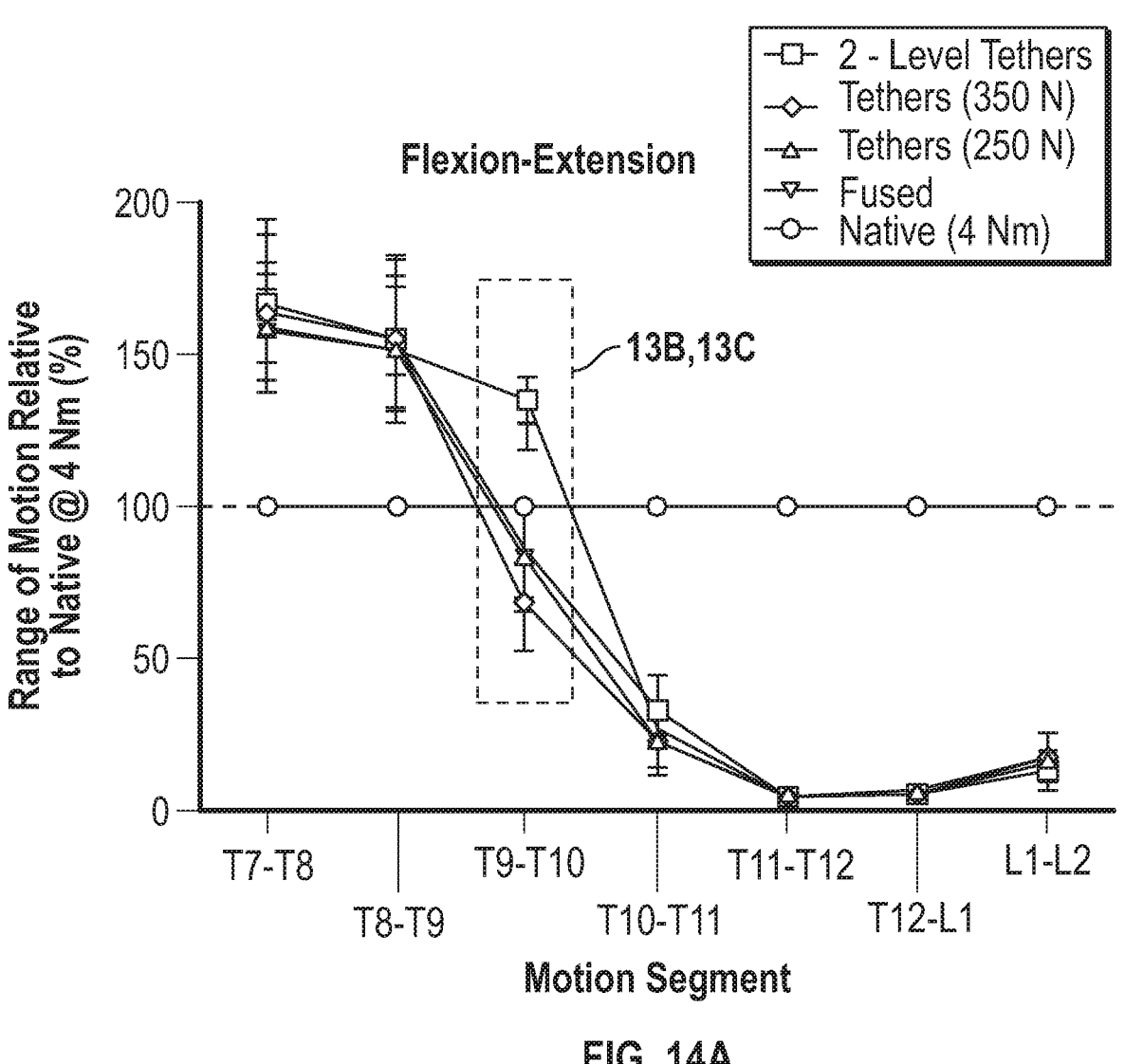
FIG. 14A is a graph that illustrates the range of motion of the motion segments under extension/flexion of different test specimens relative to a native spine loaded at 4 Nm.
Figure 14B:
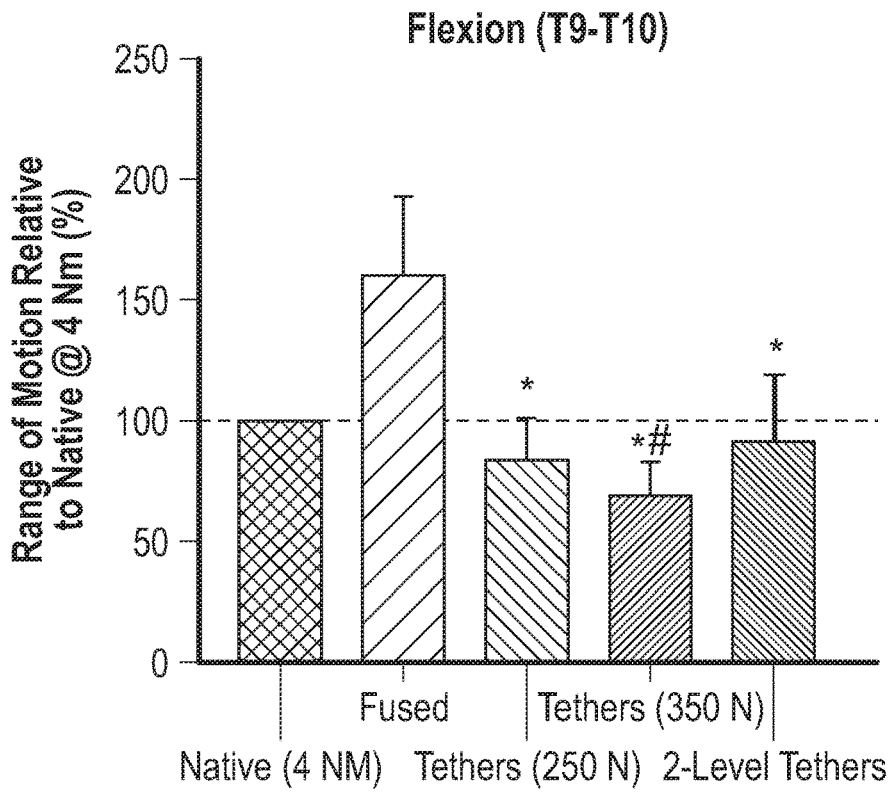
FIG. 14B shows the flexion range of motion values of the T9-T10 segments shown in FIG. 14A
Figure 14C:
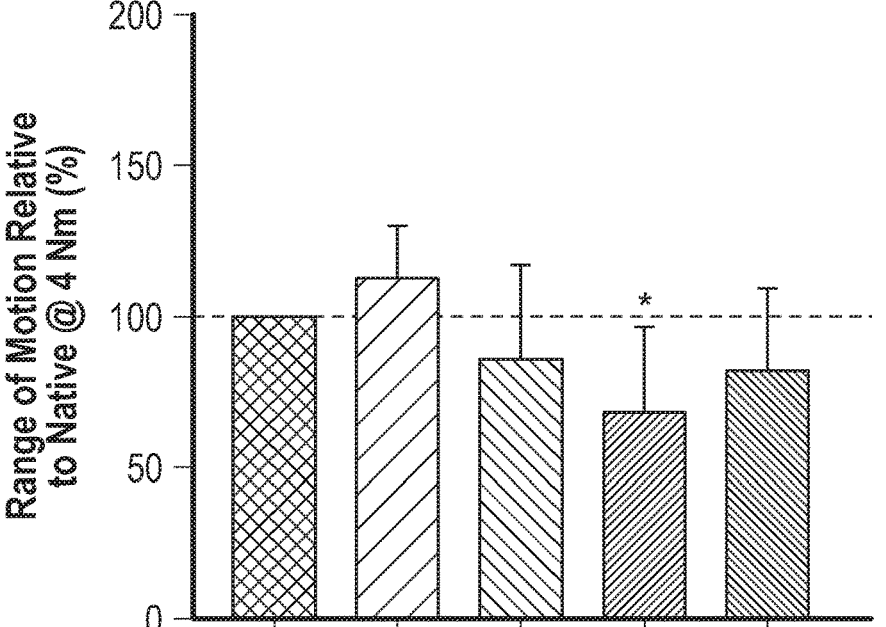
FIG. 14C shows the extension range of motion values of the T9-T10 segments shown in FIG. 14A.

With reference to FIGS. 14A-14C, the surgical interventions primarily affected the flexion and extension ROM at the index level of T9-T10. No significant differences existed between the interventions and Fused condition at T7-T8. At T8-T9, the flexion ROM was significantly increased with the Tethers at 250 N ($204\%\pm37\%$ of Native) and 350 N ($201\%\pm38\%$ of Native) compared to Fused ($176\%\pm30\%$ of Native; $p<0.05$) At T9-T10, the flexion ROM was significantly reduced from the Fused state ($162\%\pm31\%$ of Native) by Tethers at 250 N ($85\%\pm17\%$ of Native; $p<0.0001$), Tethers at 350 N ($70\%\pm14\%$ of Native; $p<0.0001$), and 2-Level Tethers ($93\%\pm28\%$ of Native; $p<0.0001$).

Tightening the tethers from 250 N to 350 N significantly reduced the flexion ROM by an additional 15% on average ($p=0.0004$). The variance associated with the Suture Loop technique was also significantly greater than Tethers at 250 N ($p<0.05$) and Tethers at 350 N ($p<0.01$). The extension ROM at T9-T10 followed the same trends as the flexion ROM.

Lateral Bending and Axial Rotation Range of Motion

Figure 15:
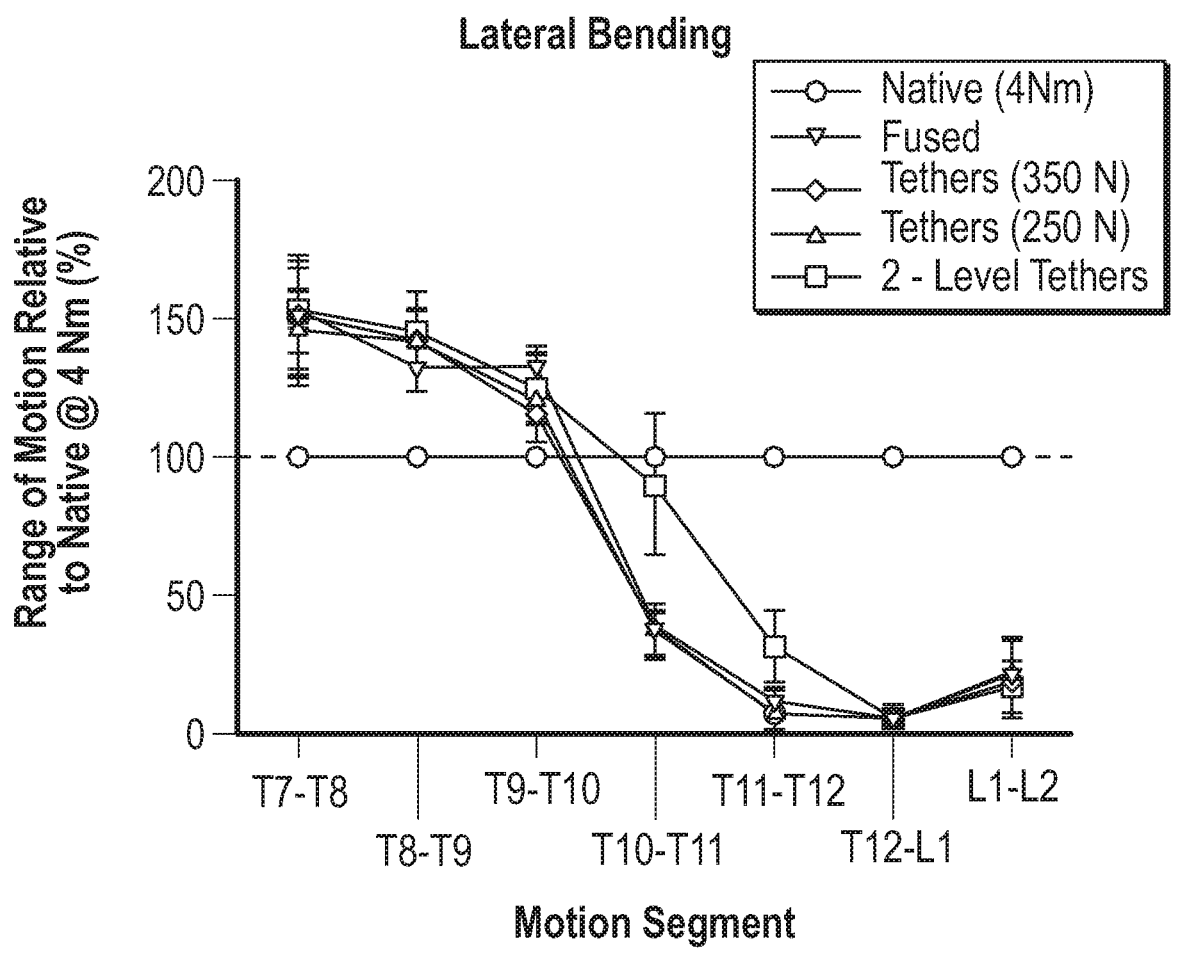
FIG. 15 is a graph that illustrates the range of motion of the motion segments under lateral bending of different test specimens relative to a native spine loaded at 4 Nm.
Figure 16:
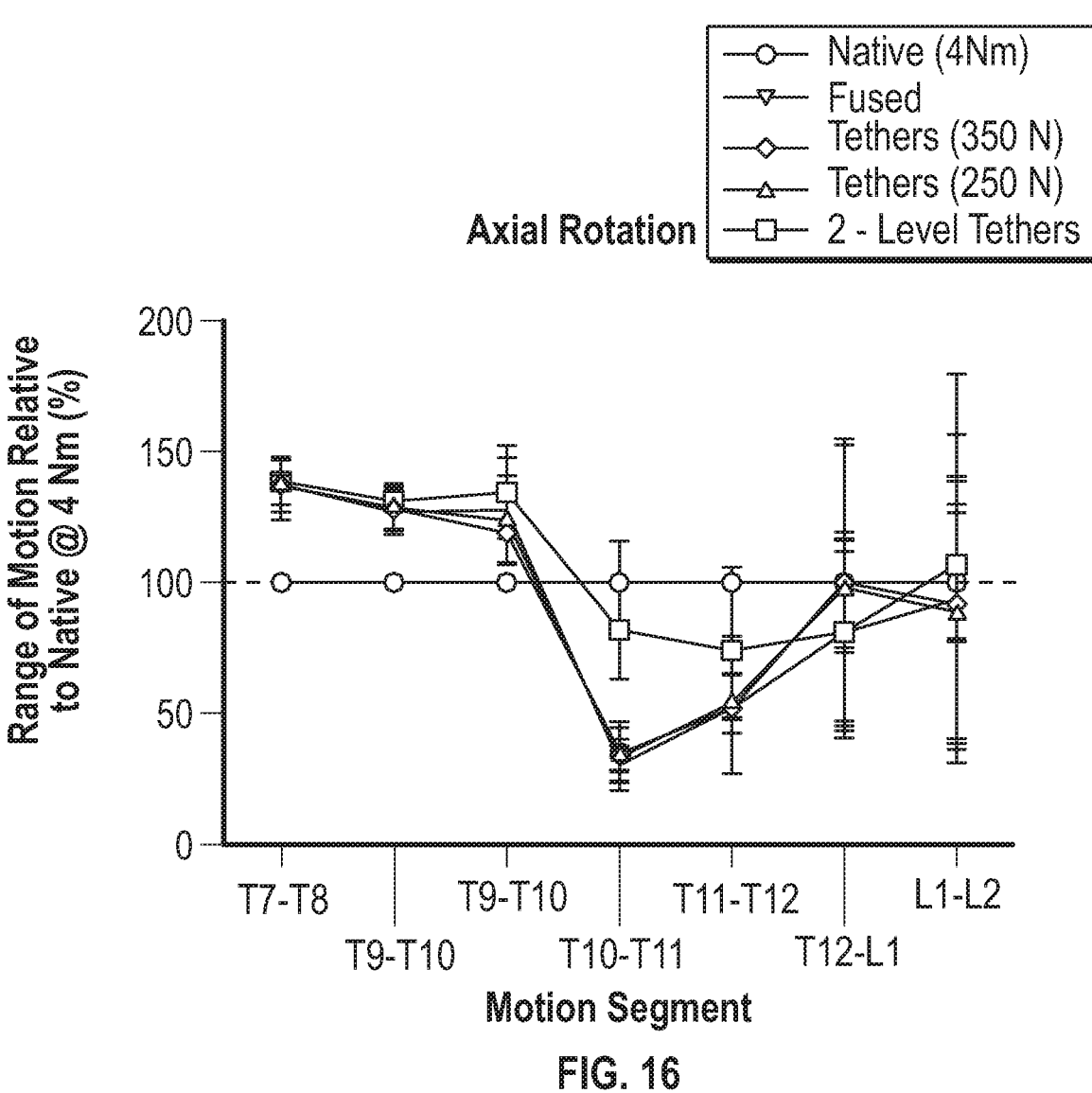
FIG. 16 is a graph that illustrates the range of motion of the motion segments under axial rotation of different test specimens relative to a native spine loaded at 4 Nm.

With reference to FIGS. 15 and 16, the bilateral pedicle screw fixation at T10-T11 with a second level of tethers created a more gradual transition in relative motion at each level from T9-T12 in lateral bending and axial rotation. The rest of the intervention techniques did not affect any of the levels across T7-L2 except for the index level (T9-T10). The ROM in lateral bending at T9-T10 was significantly reduced by Tethers at 350 N ($116\%\pm10\%$ of Native) compared to Fused ($132\%+9\%$; of Native; $p=0.009$), but no other interventions significantly affected the lateral bending ROM. Axial rotation at T9-T10 was not significantly affected by any test condition compared to Fused.

Each of these non-limiting examples and embodiments can stand on its own, or can be combined in various permutations or combinations with one or more of the other examples.

The above detailed description includes references to the accompanying drawings, which form a part of the detailed description. The drawings show, by way of illustration, specific embodiments that may be practiced. These embodiments are also referred to herein as "examples." Such examples can include elements in addition to those shown or described. However, examples are contemplated in which only those elements shown or described are provided. Moreover, embodiments are also contemplated that utilize any combination or permutation of those elements and components shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

Example 1 can include a fusion system for attenuation of increased spinal flexion loads in adjacent levels post-fusion. The fusion system can include a fusion implant and a transition member. The fusion implant can be coupleable to a plurality of fused vertebra. The transition member can include a tension component coupleable to a fused vertebra of the plurality of fused vertebra and an adjacent unfused vertebra. The tension component can be tensionable to a selected value and wherein the tension component modulates a flexion range of motion of the adjacent unfused vertebra as a function of the selected value of tension of the tension component. The transition member operates to attenuate spinal flexion loads on the adjacent unfused vertebra post-operatively.

In example 2, the subject matter of example 1 can optionally include the transition member having a clamp securable to a rod of the fusion implant and to the tension component.

In example 3, the subject matter of any one of examples 1 or 2 can optionally include the tension component being a flexible elongate member.

In example 4, the subject matter of any one of examples 1 to 3 can optionally include the tension component being coupleable to an adjacent vertebra sublaminarly.

In example 5, the subject matter of any one of examples 1 to 3 can optionally include the tension component being coupleable to a spinous process of an adjacent vertebra.

In example 6, the subject matter of any one of examples 1 to 5 can optionally include the tension component being a flexible elongate member comprised of a polyester band.

In example 7, the subject matter of any one of claims 1 to 6 can optionally include the transition member including a first bone implant coupleable to the underlying instrumented vertebra and a second bone implant coupleable to the adjacent instrumented vertebra, where the first bone implant receives a first end of the tension component and the second bone implant receives a second end of the tension component.

In example 8, the subject matter of any one of examples 1 to 5 or 7 can optionally include the tension member being a cord.

In example 9, the subject matter of example 8 can optionally include the cord being a polyester cord.

In example 10, the subject matter of any one of examples 1 to 5 or 7 can optionally include the tension member being a flexible rod.

In example 11, the subject matter of example 10 can optionally include the flexible rod being made from a polymer.

In example 12, the subject matter of any one of examples 1 to 11 can optionally include tensioning the tension member in a range of 200 N to 400 N.

In example 13, the subject matter of any one of examples 1 to 11 can optionally include tensioning the tension member in a range between 250 N and 350 N.

In example 14, the subject matter of any one of examples 1 to 13 can include adjacent unfused vertebra being cranial to the underlying instrumented vertebra.

In example 15, the subject matter of any one of examples 1 to 13 can include adjacent unfused vertebra being caudal to the underlying instrumented vertebra.

In example 16, the subject matter of any one of examples 1 to 15 can optionally include the transition member comprising a first transition member and a second transition member.

In example 17, the subject matter of example 16 can optionally include the first transition member being coupleable to the fusion implant or the underlying instrumented vertebra and the adjacent unfused vertebra on a first side of a medial plane of the spine and the second transition member being coupleable to the fusion implant or the underlying instrumented vertebra and the adjacent unfused vertebra on a second side of the medial plane of the spine.

In example 18, the subject matter of example 16 can optionally include the first transition member being coupleable to a first portion of the fusion implant or its underlying instrumented vertebra and the adjacent unfused vertebra and the second transition member being coupleable to a second portion of the fusion implant or its underlying instrumented vertebra and the adjacent unfused vertebra.

In example 19, the subject matter of example 16 can optionally include the adjacent unfused vertebra including a first adjacent unfused vertebra, where the first transition member is coupleable to a first portion of the fusion implant or its underlying instrumented vertebra and the first adjacent unfused vertebra and the second transition member is coupleable to a second portion of the fusion implant opposite the first portion or its underlying instrumented vertebra and a second adjacent unfused vertebra.

In example 20, the subject matter of any one of examples 1 to 19 can optionally include the tension component being coupleable to the underlying vertebra via coupling to the fusion implant.

In example 21, the subject matter of any one of examples 1 to 20 can optionally include the transition member being configured to attenuate proximal junction kyphosis of adjacent unfused vertebra.

In example 22, the subject matter of any one of examples 1 to 21 can optionally include the transition member being configured to attenuate distal junction kyphosis of adjacent unfused vertebra.

Example 23 is a method for treating a spine. In this example the method can include the following procedures to utilize the fusion system of any one of examples 1 to 22. The method begins by selecting a tension component of a transition member. The method continues by coupling at least a portion of the transition member to an underlying instrumented vertebra of a plurality of underlying instrumented vertebra of a fusion implant. Next the method includes coupling the tension component to the transition member. Further the method includes tensioning the tension component to a selected value. The method can continue by coupling the tension component to an adjacent unfused vertebra under the selected value of tension. The method can conclude with modulating a flexion range of motion of the adjacent unfused vertebra with the transition member as a function of the selected value of tension of the tension component.

In example 24, the subject matter of example 23 can optionally include provisionally coupling the tension component to the adjacent unfused vertebra prior to tensioning the tension component to the selected value.

In example 25, the subject matter of any one of examples 23 or 24 can optionally include provisionally coupling the tension component to the transition member prior to coupling at least a portion of the transition member to an underlying instrumented vertebra of the plurality of underlying instrumented vertebra of the fusion implant.

In example 26, the subject matter of any one of examples 23 to 25 can optionally include coupling the tension component to the transition member comprises coupling a band to a clamp.

In example 27, the subject matter of example 26 can optionally include coupling at least a portion of the transition member to an underlying instrumented vertebra of the plurality of underlying instrumented vertebra of the fusion implant further comprises coupling the clamp to a rod of the fusion implant.

In example 28, the subject matter of example 26 can optionally include coupling the tension component to the adjacent unfused vertebra further comprises sublaminarly coupling the band to the adjacent unfused vertebra.

In example 29, the subject matter of example 26 can optionally include coupling the tension component to the adjacent unfused vertebra further comprises coupling the band to a spinous process of the adjacent unfused vertebra.

In example 30, the subject matter of any one of examples 23 to 29 can optionally include tensioning the tension component to the selected value further comprises tensioning the tension component to a value of 200 to 400 N.

In example 31, the subject matter of any one of examples 23 to 29 can optionally include tensioning the tension component to the selected value further comprises tensioning the tension component to a value of 250 to 350 N.

In example 32, the subject matter of any one of examples 23 to 31 can optionally include coupling the tension component to the adjacent unfused vertebra further comprises engaging a first bone implant in the adjacent unfused vertebra and coupling a first end of the tension component to the first bone implant.

In example 33, the subject matter of example 32 can optionally include coupling at least a portion of the transition member to an underlying instrumented vertebra of the plurality of underlying instrumented vertebra of the fusion implant further comprises engaging a second bone implant in the underlying instrumented vertebra.

In example 34, the subject matter of example 33 can optionally include coupling the tension component to the transition member further comprises coupling a second end of the tension component to the second bone implant.

In example 35, the subject matter of example 32 can optionally include selecting the tension component for the tension member further comprises selecting a flexible elongate member.

In example 36, the subject matter of example 32 can optionally include selecting the tension component for the tension member further comprises selecting a flexible rod.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A fusion system, comprising:
a fusion implant capable of connecting to a plurality of fused vertebrae;
a transition member including a tension component capable of connecting to a fused vertebra of the plurality of fused vertebrae and an unfused vertebra disposed proximate the fused vertebra, the tension component comprising a flexible elongate member capable of passing through an aperture in the transition member to interface with the proximate unfused vertebra; and
a second transition member with a second tension component capable of coupling a second fused vertebra of the plurality of fused vertebrae and a second unfused vertebra positioned proximate the second fused vertebra, the second tension component comprising a second flexible elongate member capable of passing through a second aperture in the second transition member to interface with the second unfused vertebra,
wherein the tension component is tensionable to a selected value of tension by pulling a first end of the flexible elongate member through the aperture of the transition member to reduce a length of a portion of the flexible elongate member coupled to the proximate unfused vertebra;
wherein the second tension component is tensionable to a selected value of tension by pulling a first end of the second flexible elongate member through the second aperture of the transition member to reduce a length of a portion of the second flexible elongate member coupled to the second unfused vertebra;
wherein the second tension component is tensionable independently from the tension component;
wherein the tension component modulates a flexion range of motion of the proximate unfused vertebra as a function of the selected value of tension of the tension component;
wherein the transition member post-operatively attenuates spinal flexion loads on the proximate unfused vertebra; and
wherein the second tension component is positioned superior to the tension component.

2. The fusion system of claim 1, wherein the flexible elongate member comprises a tether, a cord, a band, or a flexible rod, wherein the transition member comprises a clamp and a set screw, and wherein the set screw is adjustable to secure the flexible elongate member within the clamp.

3. The fusion system of claim 2, wherein the tension component further comprises a bone implant, and wherein the bone implant is configured to engage with the fused vertebra.

4. The fusion system of claim 3, wherein a first end of the tension component is received by the bone implant after the tension component has been tensioned to the selected value of tension.

5. The fusion system of claim 2, wherein the set screw is further adjustable to secure the clamp to a bone implant.

6. The fusion system of claim 5, wherein the bone implant comprises a vertebral rod.

7. The fusion system of claim 1, wherein the flexible elongate member is configured to be looped around at least a portion of the proximate unfused vertebra.

8. A system, comprising:

a first transition member including a first tension component capable of connecting to a first fused vertebra of a plurality of fused vertebrae and a first unfused vertebra positioned proximate the first fused vertebra, the first tension component comprising a first flexible elongate member capable of passing through a first aperture in the first transition member to interface with the first unfused vertebra; and a second transition member with a second tension component capable of connecting to a second fused vertebra of the plurality of fused vertebrae and a second unfused vertebra positioned proximate the second fused vertebra, the second tension component comprising a second flexible elongate member capable of passing through a second aperture in the second transition member to interface with the second unfused vertebra, wherein the first tension component is tensionable to a selected value of tension by pulling a first end of the first flexible elongate member through the first aperture of the first transition member to reduce a length of a portion of the first flexible elongate member coupled to the first unfused vertebra;

wherein the second tension component is tensionable to a selected value of tension by pulling a first end of the second flexible elongate member through the second aperture of the second transition member to reduce a length of a portion of the second flexible elongate member coupled to the second unfused vertebra; and wherein the second tension component is tensionable independently from the first tension component.

9. The system of claim 8, wherein the first transition member comprises a clamp and a set screw, and wherein the set screw is adjustable to secure the first flexible elongate member within the clamp.

10. The system of claim 9, wherein the first flexible elongate member comprises a tether, a cord, a band, or a flexible rod.

11. The system of claim 10, wherein the first tension component further comprises a bone implant, and wherein the bone implant is configured to engage with the first fused vertebra.

12. The system of claim 8, wherein the first tension component modulates a flexion range of motion of the first unfused vertebra as a function of the selected value of tension of the first tension component.

* * * * *